United States Patent
Chan

(10) Patent No.: US 7,318,939 B2
(45) Date of Patent: Jan. 15, 2008

(54) HERBAL FORMULATION FOR TREATMENT OF DEPRESSION AND OTHER RELATED DISORDERS AND METHOD OF PREPARING THE SAME

(75) Inventor: Hei Ling Helen Chan, Hong Kong (CN)

(73) Assignee: Vita Green Health Products Co., Ltd., Hong Kong SAR (CN)

( * ) Notice: Subject to any disclaimer, the term of this patent is extended or adjusted under 35 U.S.C. 154(b) by 0 days.

(21) Appl. No.: 11/429,247

(22) Filed: May 8, 2006

(65) Prior Publication Data

US 2007/0258995 A1 Nov. 8, 2007

(51) Int. Cl.
*A61K 36/00* (2006.01)
*A61K 9/00* (2006.01)

(52) U.S. Cl. ..................... 424/725; 424/400
(58) Field of Classification Search ............... 424/725
See application file for complete search history.

(56) References Cited

OTHER PUBLICATIONS

Guo et al. (2004). Antidepressant Evaluation of Polysaccharides from a Chinese Herbal Medicine Banxia-houpu Decoction. Phytother, Res. 18, p. 204-207.
Yu et al. (2002). Antidepressant activity of aqueous extracts of *Curcuma longa* in mice. Journal of Ethnopharmacoogy 83 p. 161-165.
Hong Kong Registration of Proprietary Chinese Medicines Application Handbook.
Relevant pages from the Pharmacopoeia of the People's Republic of China (2005), English translation.
Hsu, et al. (1996). Oriental Materia Medica: A Concise Guide. Keats Pub. Long Beach. p. 626-627.
Hsu, et al. (1996). Oriental Materia Medica: A Concisie Guide. Keats Pub. Long Beach. p. 632-633.
Bensky, D. et al. (1993). Chinese Herbal Medicine: Materia Medica, Revised ed. Eastland Press. Washington. p. 390-391.
Bensky, D. et al. (1993). Chinese Herbal Medicine: Materia Medica, Revised ed. Eastland Press. Washington. p. 397-399.

*Primary Examiner*—Christopher R Tate
*Assistant Examiner*—Randall Winston
(74) *Attorney, Agent, or Firm*—Eagle IP Limited; Jacqueline C. Lui

(57) ABSTRACT

A herbal formulation used for treatment of depression and other related disorders comprises the following ingredients, namely Os Draconis, Concha Ostreae, Fructus Tritici Aestivi, Bulbus Lilii, Radix Rehmanniae, Caulis Polygoni Multiflori, Fructus Jujubae, Flos Albiziae, Radix Et. Rhizoma Glycyrrhizae Praeparata Cum Melle, Sclerotium Poriae Circum Radicem Pini, Caulis Bambusae in Taenia, and Rhizoma Zingiberis Recens.

23 Claims, 4 Drawing Sheets

HERBAL FORMULATION FOR TREATMENT OF DEPRESSION AND OTHER RELATED DISORDERS AND METHOD OF PREPARING THE SAME

FIELD OF INVENTION

This invention relates to a herbal formulation and in particular a formulation for treatment of depression and other related disorders. This invention also relates to methods for preparing such herbal formulation.

BACKGROUND OF INVENTION

Depression, in general, refers to a state of sadness in which the affected individuals have experienced different degrees of disruption in their social functioning and their daily activities depending on the seriousness of the situation. Common symptoms may include loss of interest, feelings of overwhelming sadness or fear, changing of appetite with marked variations in body weights, and decrease in self-esteem.

Medication and psychotherapy are the two typical methods for treating depression, and these two methods are usually employed in conjunction with one another. Tricyclic antidepressants (TCA), selective serotonin reuptake inhibitors (SSRI) and monoamine oxidase inhibitors (MAOI) are the drugs that have found broad usages in treating depression. However, adverse side effects may accompany the use of these drugs, such as sexual dysfunction and the additive dependence on drugs leading to drug abuse.

SUMMARY OF INVENTION

In the light of the foregoing background, it is an object of the present invention to provide a herbal formulation as an alternative for treatment of depression and other related disorders.

Accordingly, the present invention, in one aspect, provides a herbal formulation comprising the following ingredients: Fructus Tritici Aestivi, Bulbus Lilii, Radix Rehmanniae, Caulis Polygoni Multiflori, Fructus Jujubae, Flos Albiziae, Sclerotium Poriae Circum Radicem Pini, and Rhizoma Zingiberis Recens.

In a more preferred embodiment, the herbal formulation further comprises at least one additional component of Os Draconis, Concha Ostreae, Caulis Bambusae in Taenia, or Radix Et. Rhizoma Glycyrrhizae Praeparata Cum Melle.

In a preferred embodiment of the present invention, the herbal formulation is used for treatment of depression or anxiety disorders.

In another preferred embodiment, the composition of the herbal formulation is listed in Table 2, in which the ingredients in the formulation are in such an amount that it provides the highest efficacy for treatment of depression or anxiety disorders.

According to another aspect of the present invention, a method is provided for preparing the herbal formulation with the ingredients described above which comprises extracting the ingredients with boiling water and concentrating the extract to form an oral formulation.

In one implementation of the above method, a further step of extracting is provided in which an initial herbal mixture of Os Draconis and Concha Ostreae is first boiled, simmered and extracted under circulation for 1 to 2 hours, followed by another step of boiling, simmering and extracting under circulation of a herbal mixture of the remaining ingredients, namely Fructus Tritici Aestivi, Bulbus Lilii, Radix Rehmanniae, Caulis Polygoni Multiflori, Fructus Jujubae, Flos Albiziae, Radix Et. Rhizoma Glycyrrhizae Praeparata Cum Melle, Sclerotium Poriae Circum Radicem Pini, Caulis Bambusae in Taenia, and Rhizoma Zingiberis Recens, with the initial herbal mixture for 1 to 3 hours.

In yet another implementation of the method, the herbal mixture is further boiled, simmered and extracted under circulation for 0.5 to 2 hours.

In the most preferred implementation of the method, the concentrating step further comprises the steps of concentrating the extract under reduced pressure; mixing the concentrated extract with an excipient; drying the mixture by vacuum; grinding the dried mixture into powder; and sieving the powder to obtain fine powder. In the most preferred embodiment, the excipient is Dextrin.

In another implementation of the method of the present invention, a method of preparing the herbal formulation with aforementioned ingredients contains the steps of boiling, simmering and extracting under circulation of the initial herbal mixture of Os Draconis and Concha Ostreae for 1.5 hours; boiling, simmering and extracting under circulation of the herbal mixture of the remaining ingredients, namely Fructus Tritici Aestivi, Bulbus Lilii, Radix Rehmanniae, Caulis Polygoni Multiflori, Fructus Jujubae, Flos Albiziae, Radix Et. Rhizoma Glycyrrhizae Praeparata Cum Melle, Sclerotium Poriae Circum Radicem Pini, Caulis Bambusae in Taenia, and Rhizoma Zingiberis Recens, with the initial herbal mixture for 2 hours; boiling, simmering and extracting under circulation of the herbal mixture for 1 hour; concentrating the extract under reduced pressure; mixing the concentrated extract with Dextrin; drying the mixture by vacuum; grinding the dried mixture into powder; and sieving the powder to obtain fine powder.

DETAILED DESCRIPTION OF THE PREFERRED EMBODIMENTS

Figure 1:
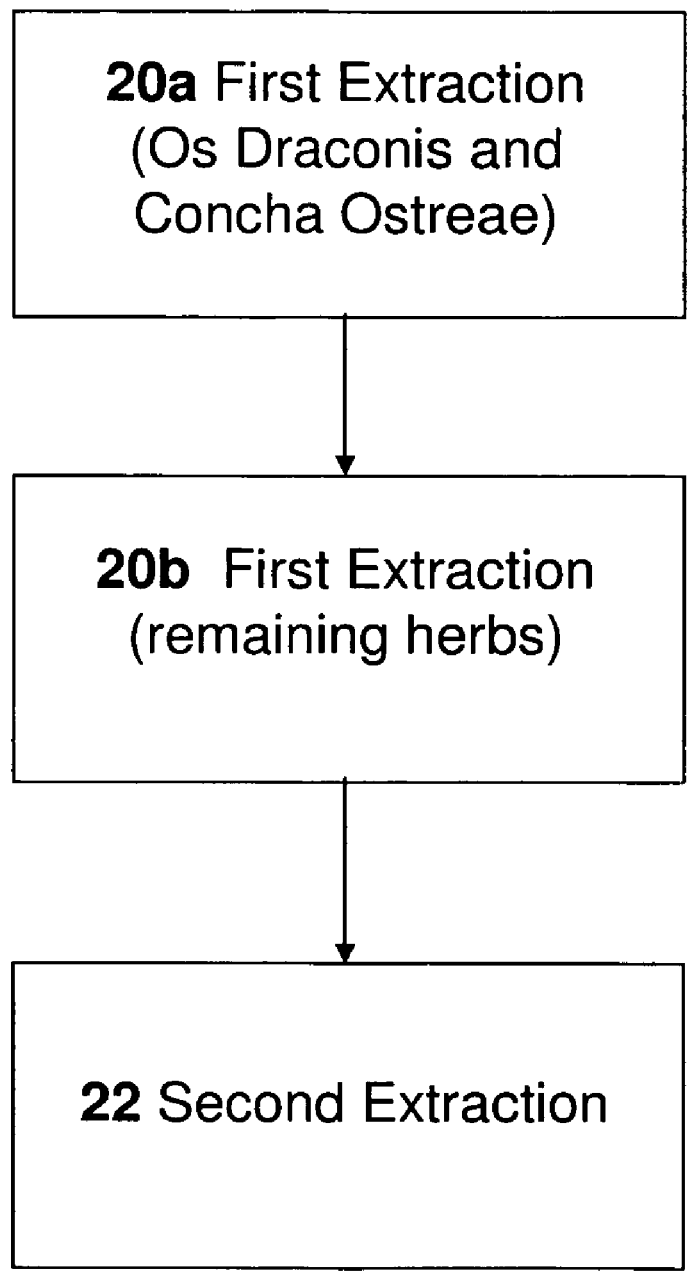
FIGS. 1 and 2 are outlines of the extraction and concentration processes respectively for preparing the herbal formulation for treatment of depression and other related disorders according to one embodiment of the present invention.

As used herein and in the claims, "comprising" means including the following elements but not excluding others. The process of "boiling" refers to the process of heating the herbs with water to a high temperature, generally at 100° C.±5° C. The process of "simmering" refers to heating the herbs with water and keeping the heated content at temperatures between 90° C. and 100° C.

The present invention provides a herbal formulation with ingredients of one specific preferred embodiment listed in Table 1 below by medicinal name, corresponding processed form, common name, related herbs and alternative names.

TABLE 1

| Medicinal Name | Processed Form | Common Name | Related herb(s) | Alternative Name |
|---|---|---|---|---|
| 1. 生龍骨 Os Draconis | 煅龍骨 Os Draconis (calcined) | 龍骨 Os Draconis | 龍齒 Dens Draconis 及炮製品 | — |
| 2. 生牡蠣 Concha Ostreae | 煅牡蠣 Concha Ostreae (calcined) | 牡蠣 Concha Ostreae | — | — |
| 3. 淮小麥 Fructus Tritici Aestivi | — | 小麥 Fructus Tritici Aestivi | 浮小麥 Fructus Tritici Levis | — |
| 4. 百合 Bulbus Lilii | 蜜百合/炙百合 Bulbus Lilii (Stir-baked with honey) | 百合 Bulbus Lilii | — | — |
| 5. 生地 Radix Rehmanniae | 熟地/熟地黃 Radix Rehmanniae Preparata | 地黃 Radix Rehmanniae | — | 鮮地黃/生地黃/干 地黃 Radix Rehmanniae |
| 6. 首烏藤 Caulis Polygoni Multiflori | — | 首烏藤 Caulis Polygoni Multiflori | — | 夜交藤 Caulis Polygoni Multiflori |
| 7. 大棗 Fructus Jujubae | — | 大棗 Fructus Jujubae | — | — |
| 8. 合歡花 Flos Albiziae | — | 合歡花 Flos Albiziae | 合歡皮 Cortex Albiziae | — |
| 9. 炙甘草 Radix Et. Rhizoma Glycyrrhizae Praeparata Cum Melle* | — | 炙甘草 Radix Et. Rhizoma Glycyrrhizae Praeparata Cum Melle | 甘草/粉甘草 Radix Et. Rhizoma Glycyrrhizae | 蜜甘草 Radix Glycyrrhizae Preparata |
| 10 茯神 Sclerotium Poriae Circum Radicem Pini | — | 茯神 Sclerotium Poriae Circum Radicem Pini | 茯苓/茯苓皮 Poria | — |
| 11. 竹茹 Caulis Bambusae in Taenia | 姜竹茹 Caulis Bambusae in Taenia (Stir-baked with ginger juice) | 竹茹 Caulis Bambusae in Taenia | — | 淡竹茹 Caulis Bambusae in Taenia |
| 12. 生姜 Rhizoma Zingiberis Recens | 乾姜 Rhizoma Zingiberis 炮姜 Rhizoma Zingiberis Praeparatum | 生姜 Rhizoma Zingiberis Recens | 乾姜 Rhizoma Zingiberis | — |

The individual components in the formulation according to the present invention and as used in the claims are generally referred by the medicinal names of the herbs (column 2 in Table 1) as the preferred embodiment, but the processed forms (column 3 of Table 1) and the related herbs (column 5 of Table 1) may be used as substitutes or equivalents.

(* The name in ingredient 9, Radix Et. Rhizoma Glycyrrhizae Praeparata Cum Melle, is taken from the 2005 edition of the Pharmacopoeia of the People's Republic of China. Ingredient 9 has an alternative name of Radix Glycyrrhizae Preparata in the older version(s) of the Pharmacopoeia of the People's Republic of China. Similarly, its unprocessed form, Radix Et. Rhizoma Glycyrrhizae, has an alternative name of Radix Glycyrrhizae in the older version(s) of the Pharmacopoeia of the People's Republic of China. This unprocessed form may be used as a substitute or equivalent and the term Rhizoma Glycyrrhizae Praeparata Cum Melle should be interpreted to mean either the processed or unprocessed form.)

In a more preferred embodiment, the composition of the herbal formulation uses the medicinal herbs as shown in column 2 of Table 1 is listed in Table 2 below.

TABLE 2

| No. | Herb | Composition (kg) | By weight % |
|---|---|---|---|
| 1 | Os Draconis | 30 | 10 |
| 2 | Concha Ostreae | 30 | 10 |
| 3 | Fructus Tritici Aestivi | 60 | 20 |
| 4 | Bulbus Lilii | 30 | 10 |
| 5 | Radix Rehmanniae | 30 | 10 |
| 6 | Caulis Polygoni Multiflori | 30 | 10 |
| 7 | Fructus Jujubae | 30 | 10 |
| 8 | Flos Albiziae | 18 | 5 |
| 9 | Radix Et. Rhizoma Glycyrrhizae Praeparata Cum Melle | 18 | 5 |
| 10 | Sclerotium Poriae Circum Radicem Pini | 12 | 4 |
| 11 | Caulis Bambusae in Taenia | 9 | 3 |
| 12 | Rhizoma Zingiberis Recens | 9 | 3 |
| | Total | 306 | 100 |

Figure 2:
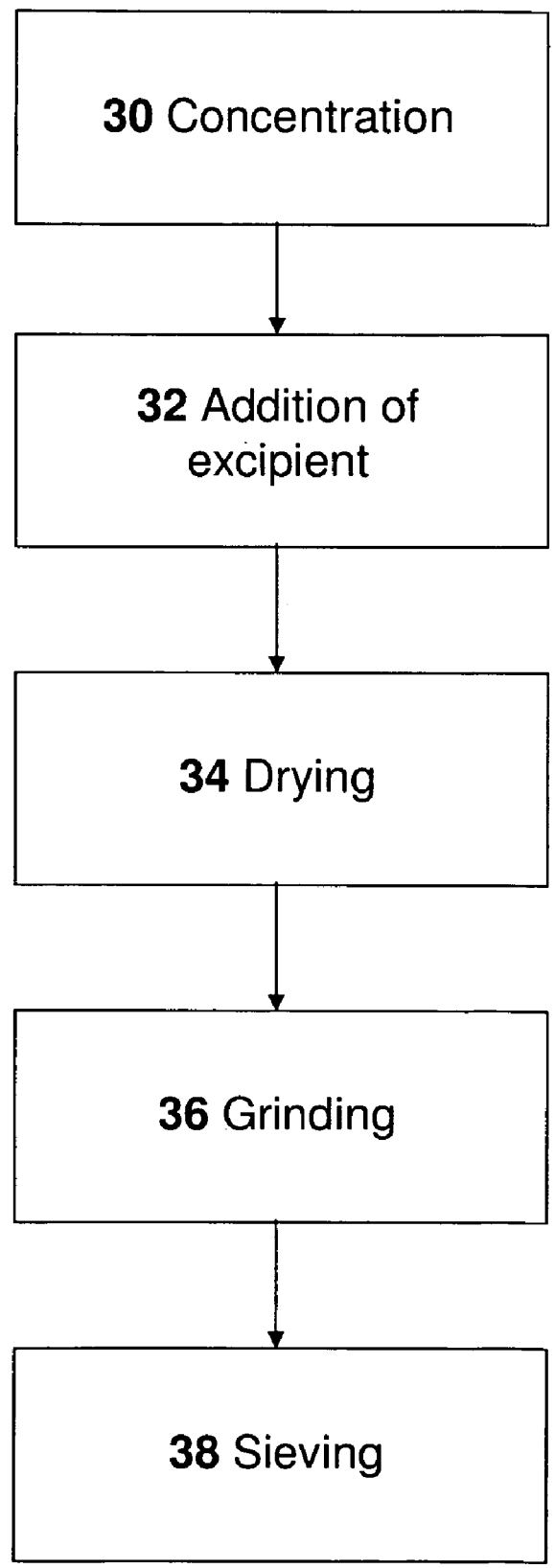

FIGS. 1 and 2 outline the major steps for preparing the herbal formulation according to the present invention.

Referring first to FIG. 1, steps for extracting the above-mentioned herbs are provided. In the initial step of the first extraction 20a, powders of Os Draconis and Concha Ostreae are put into the percolator in separate cloth sacks respectively according to the extraction post procedures. The percolator is then filled with water at a ratio of 1:6, total ingredients:water, and heated to boiling (i.e. for each 100 kg total ingredients, 600 liters water is used). The heated initial herbal mixture is then simmered between 90° C. and 100° C. and extracted under circulation for 1.5 hours. Upon cooling to 50° C., the remaining herbs, namely Fructus Tritici Aestivi, Bulbus Lilii, Radix Rehmanniae, Caulis Polygoni Multiflori, Fructus Jujubae, Flos Albiziae, Radix Et. Rhizoma Glycyrrhizae Praeparata Cum Melle, Sclerotium Poriae Circum Radicem Pini, Caulis Bambusae in Taenia, and Rhizoma Zingiberis Recens, are put into the percolator and soaked for 30 minutes in the final step of the first extraction 20b. The herbal mixture is then heated again to boiling and is simmered between 90° C. and 100° C. and extracted under circulation for 2 hours. During this circulation process, the herbal mixture is cycled every 15 minutes, with 10 minutes for each cycle. Afterwards, the herbal mixture is filtered into the first filtrate and the first residue.

In the second extraction step 22, the first residue is heated with water at a ratio of 1:5, total ingredients:water, (i.e. for each 100 kg total ingredients, 500 liters water is used) to boiling, simmered between 90° C. and 100° C. and extracted under circulation for one hour. Again, in this heating process, the mixture is cycled every 15 minutes, with 10 minutes for each cycle. The mixture is then filtered and the filtrate is mixed with the first filtrate.

The steps for concentrating the extract from the above-described extraction are shown in FIG. 2. In the concentration step 30, the mixed filtrate is concentrated under reduced pressure according to the concentration post procedures as a moist paste, with a relative density of between 1.10 and 1.30 at 55° C. to 65° C. In a more preferred embodiment, the relative density of the moist paste is between 1.25 and 1.30. The moist paste is then mixed with an excipient (step 32), stirred and dried by vacuum (step 34). In the most preferred embodiment, the exceipient is Dextrin. The dried paste with a moisture content of less than 5% is collected. Afterwards, the dried paste is ground by hammer mill (step 36), followed by a sieving step 38 in which the paste is passed through an 80 mesh sieve into fine powder as the final product of oral formulation.

The present invention is further defined by the following examples, which are not intended to limit the present invention.

EXAMPLE 1

Thin Layer Chromatography Analysis

Five grams of each of the three batches of the herbal formulation, with composition listed in Table 2, were added with 40 mL methanol. The mixed solution was then extracted by ultrasound for 15 minutes and filtered. The filtrate was evaporated. The filtrate residue was dissolved in 10 mL ethyl acetate and filtered again. Upon evaporation of the filtrate, the filtrate residue was further dissolved in 1 mL ethyl acetate and the resulting solution was used as the specimen. 1 mg/1 mL emodin reference solution in methanol was used as the control. The Thin Layer Chromatography analysis is performed with reference to The Pharmacopoeia of the People's Republic of China 2000, Volume I, Appendix VI B. 10 µL of each of the three specimens and the control were dotted on a thin plate of Silica Gel G using carboxymethylcellulose sodium as binder. The samples on the plate were then developed by the upper layer of methylbenzene: ethyl acetate:formic acid (40:4:3) as the mobile phase. Upon drying, the thin plate was detected under ultraviolet light of wavelength 365 nm.

Figure 3:
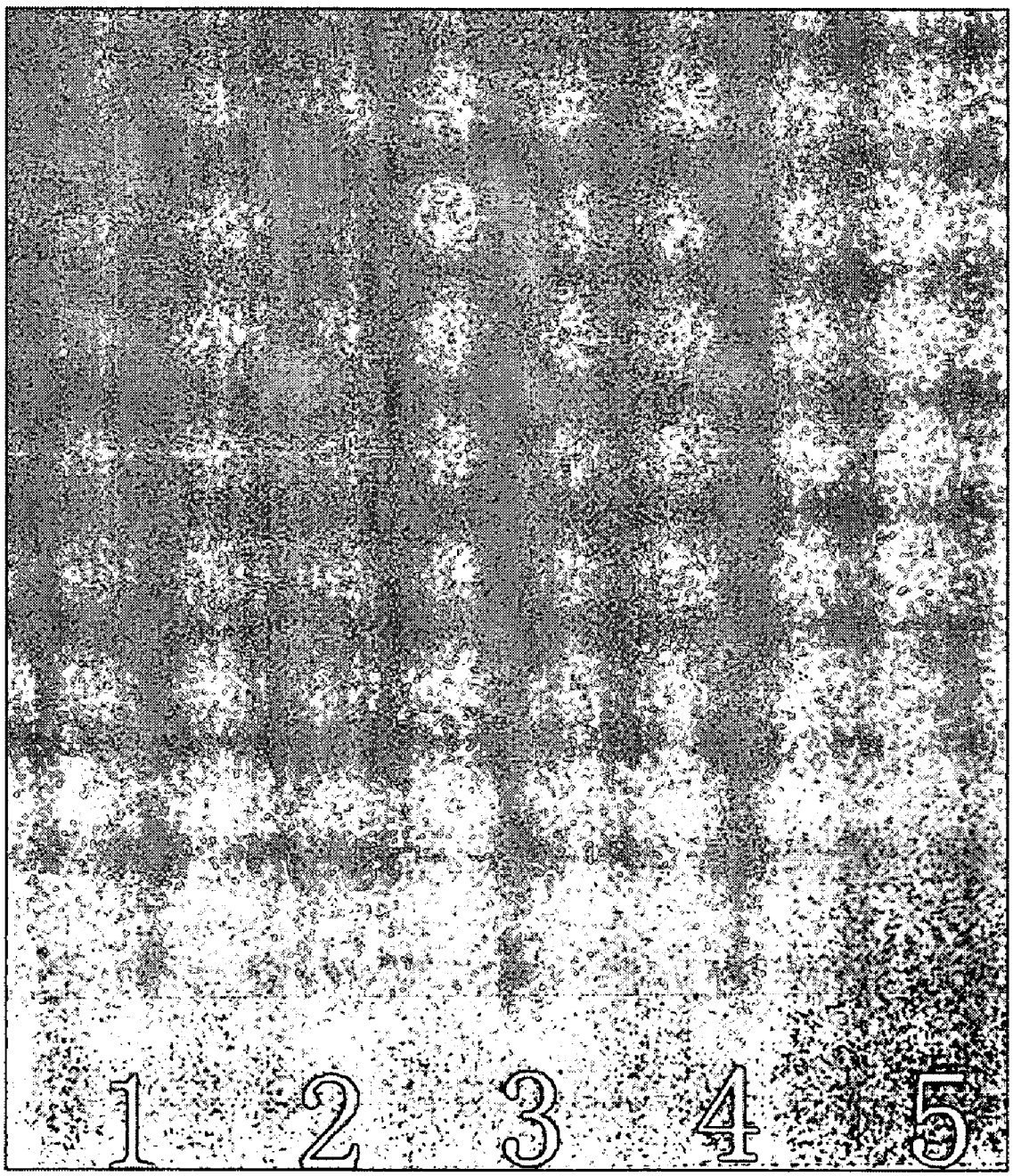
FIG. 3 is an image of a thin layer chromatography plate after developing the present formulation with methylbenzene:ethyl acetate:formic acid (40:4:3) under ultraviolet light.

The result is shown in FIG. 3 in which the three specimens are numbered 1-3, while the control is dotted on the silica plate as No. 4. It can be observed that all the three specimens have identical spots with the same fluorescence color as those from the control at the relevant position on the silica plate, indicating that the three batches tested have high reproducibility and good stability.

EXAMPLE 2

Oral Acute Toxicity Test

Forty ICR mice, male quasi, weighing 18-20 g at the start of the study were obtained from Beijing Victoria-Oliver's Animals Technology, Ltd. The mice were fasted for 14 hours before the start of the experiment.

The mice were divided into control group and test group. A volume of 0.4 mlL/10 g body weight (BW) herbal formulation was administrated to the mice in the test group by gastric gavage route. The administrated solution was prepared by dissolving powders of the herbal formulation, with compositions listed in Table 2, in deionized water in a concentration of 0.357 g/mL. The control group only received the same volume of deionized water by the same route. The reactions of mice including appearance, action of limbs, intake of food, intake of water and excretion were immediately observed after administration. These observations were made daily with the mice being weighed once every 2 days for 7 consecutive days. The reactions of the mice were recorded in details in Table 3 below.

TABLE 3

| Group | Gender | Number | BW before administration (g) X ± SD | BW after administration (g) X ± SD | Reaction of mice after administration | | | | | |
|---|---|---|---|---|---|---|---|---|---|---|
| | | | | | Appearance | Action of limbs | Intake of food | Intake of water | Excretion | Death |
| Control group | M | 10 | 19.4 ± 0.5 | 29.1 ± 1.5 | — | — | — | — | — | 0 |
| | F | 10 | 18.9 ± 0.6 | 24.4 ± 0.6 | — | — | — | — | — | 0 |
| Test group | M | 10 | 19.2 ± 0.6 | 27.3 ± 2.8 | — | — | — | — | — | 0 |
| | F | 10 | 18.9 ± 0.4 | 23.6 ± 1.3 | — | — | — | — | — | 0 |

Note:
"—" represents normal.

The results showed that after 7 consecutive days of observations, abnormality was not found in the reactions of the animals, including appearance, action of limbs, intake of food, intake of water and excretion, after administration. All of the mice survived healthily with increased body weights. The difference between the test group and the control group was not significant (P>0.05); toxicity reaction was not observable by naked eyes.

EXAMPLE 3

Pesticide Residue Test

The analysis was performed by the in-house method TCM PEST1-001 of SGS Hong Kong Ltd., employing solvent extraction of the sample from the herbal formulation with composition listed in Table 2, followed by the gas chromatography-mass chromatography measurement. This method was accredited by The Hong Kong Laboratory Accreditation Scheme, equivalent to the international lab standard ISO 17025.

TABLE 4

| Pesticides Residue | Results (mg/kg, or ppm) | Maximum Permitted Level (mg/kg) |
| --- | --- | --- |
| Aldrin & Dieldrin | <0.02 | 0.05 |
| Chlordane (sum of cis-, trans-, & oxychlordane) | <0.03 | 0.05 |
| DDT (sum of p,p'-DDT, o,p'-DDT, p,p'-DDE & p,p'-TDE) | <0.10 | 1.00 |
| Endrin | <0.01 | 0.05 |
| Heptachlor (Heptachlor & Heptachlorepoxide) | <0.02 | 0.05 |
| Hexachlorobenzene | <0.02 | 0.10 |
| Hexachlorocyclohexane isomers (other than gamma) | <0.21 | 0.30 |
| Lindane | <0.06 | 0.60 |
| Quintozene (sum of quintozene, pentachloroaniline and methyl pentachlorophenyl sulphide) | <0.05 | 1.00 |

Table 4 above shows the result of this test, indicating that the extracted concentrations of all the pesticide residues under analysis are below the maximum permitted level set forth by the Department of Health of the Government of the Hong Kong Special Administrative Region, with reference to the international standards.

EXAMPLE 4

Heavy Metal and Toxic Elements Test

The analysis was preformed by the in-house method TCM HM1-001 of SGS Hong Kong Ltd., employing the digestion of the sample from the herbal formulation with composition listed in Table 2, in acid mixture, followed by the inductively-coupled argon plasma spectrometry measurement. This method was accredited by The Hong Kong Laboratory Accreditation Scheme, equivalent to the international lab standard ISO 17025.

TABLE 5

| Heavy Metal and Toxic Elements | Results | | Maximum Permitted Level (total intake) |
| --- | --- | --- | --- |
| Arsenic (as) | 0.4 mg/kg (ppm) | 1 µg/day* | 1500 µg/day |
| Cadmium (Cd) | <0.04 mg/kg (ppm) | <0.04 µg/dose* | 3500 µg/dose |
| Lead (Pb) | <1 mg/kg (ppm) | <3 µg/day* | 179 µg/day |
| Mercury (Hg) | <0.1 mg/kg (ppm) | <0.3 µg/day* | 36 µg/day |

The data was calculated based on the maximum dosage given by the client: 500 mg/unit, 2 unit/dose, 3 dose/day From the result shown in Table 5 above, it can be observed that the extracted concentrations of all the heavy metal and toxic elements are below the maximum permitted level set forth by the Department of Health of the Government of the Hong Kong Special Administrative Region, with reference to the international standards.

EXAMPLE 5

Microbial Examination

The analysis was performed using sample from the herbal formulation with composition listed in Table 2 with reference to The Pharmacopoeia of the People's Republic of China 2000, Volume I, Appendix XIII C. This method was accredited by The Hong Kong Laboratory Accreditation Scheme, equivalent to the international lab standard ISO 17025.

TABLE 6

| Microbiological examination | Results | Microbial limits (per g or per ml) |
| --- | --- | --- |
| Aerobic Bacteria Count | 110 colony/g | 1000 |
| Mold & Yeast Count | | |
| Mould Count | <10 colony/g | 100 |
| Yeast Count | <10 colony/g | 100 |
| *Escherichia coli* | Absent/g | — |

Note:
— stands for not detecting in per g or per ml.

Table 6 above shows the result of this test, indicating that the quantity of micro-organisms present is below the microbial limits set forth by the Department of Health of the Government of the Hong Kong Special Administrative Region, with reference to the international standards.

EXAMPLE 6

Anti-depressant Activity: Forced Swimming Test in Mice

A depressed state can be induced in mice by forcing them to swim in a narrow cylinder from which they cannot escape. After an initial period of vigorous activity, the mice adopt a characteristic immobile posture which is readily identifiable. A reduction in this immobility is observed after previous administration of several antidepressant treatments. Due to its procedural simplicity and its high reproducibility, this method has become a standard antidepressant test in pharmacology.

The test item was the herbal formulation as described in Table 2 prepared by the methods shown in FIGS. 1 and 2 in the form of a powder. The reference item was Imipramine hydrochloride (Imipramine HCl) supplied by Sigma-Aldrich Quimica, S. A.

Fifty-five male CD1 mice weighing 20-25 g at the start of the study were obtained from Charles River Laboratories España (Barcelona, Spain). These mice underwent a prior acclimatization period of 6 days before the start of the experimental work, during which they underwent a veterinary examination in order to assure their good health.

The mice were allotted at random to five groups, each consisting of ten animals. The rest of the animals (one per group) were kept as reserve (these animals are not taken into account in the final results). The experimental design is described in the Table 7 below.

TABLE 7

| Group | Treatment | Dose | Route | Color Code |
|---|---|---|---|---|
| A | Control | — | po | White |
| B | Imipramine HCl | 30 mg/kg | ip | Yellow |
| C | Herbal Formulation | 100 mg/kg | po | Blue |
| D | Herbal Formulation | 200 mg/kg | po | Green |
| E | Herbal Formulation | 300 mg/kg | po | Red |

The mice began a fasting period of approximately 6 hours before starting the treatments. At the beginning of the test, the corresponding treatments were administrated by the assigned route at a volume of 10 mL/kg. The test item was administrated at three dose levels of 100, 200 and 300 mg/kg by oral route (gastric gavage or po). The reference item was administrated at the dose level of 30 mg/kg by intraperitoneal route or ip. The Control group only received the vehicle (water for injection) orally (po) by gastric gavage.

Six minutes after the administration of the treatments, each mouse was dropped into the cylinder containing water (forcing it to swim) and left there for 6 minutes, the testing time. The time of immobility of the animal was recorded. A mouse was considered immobile when it ceased struggling and remained floating motionless in the water making only those movements necessary to keep its head above water. Since little immobility was observed during the first 2 minutes, only that occurring during the last 4 minutes was measured. Finally, once the test was over, the animals were sacrificed by cervical dislocation.

Figure 4:
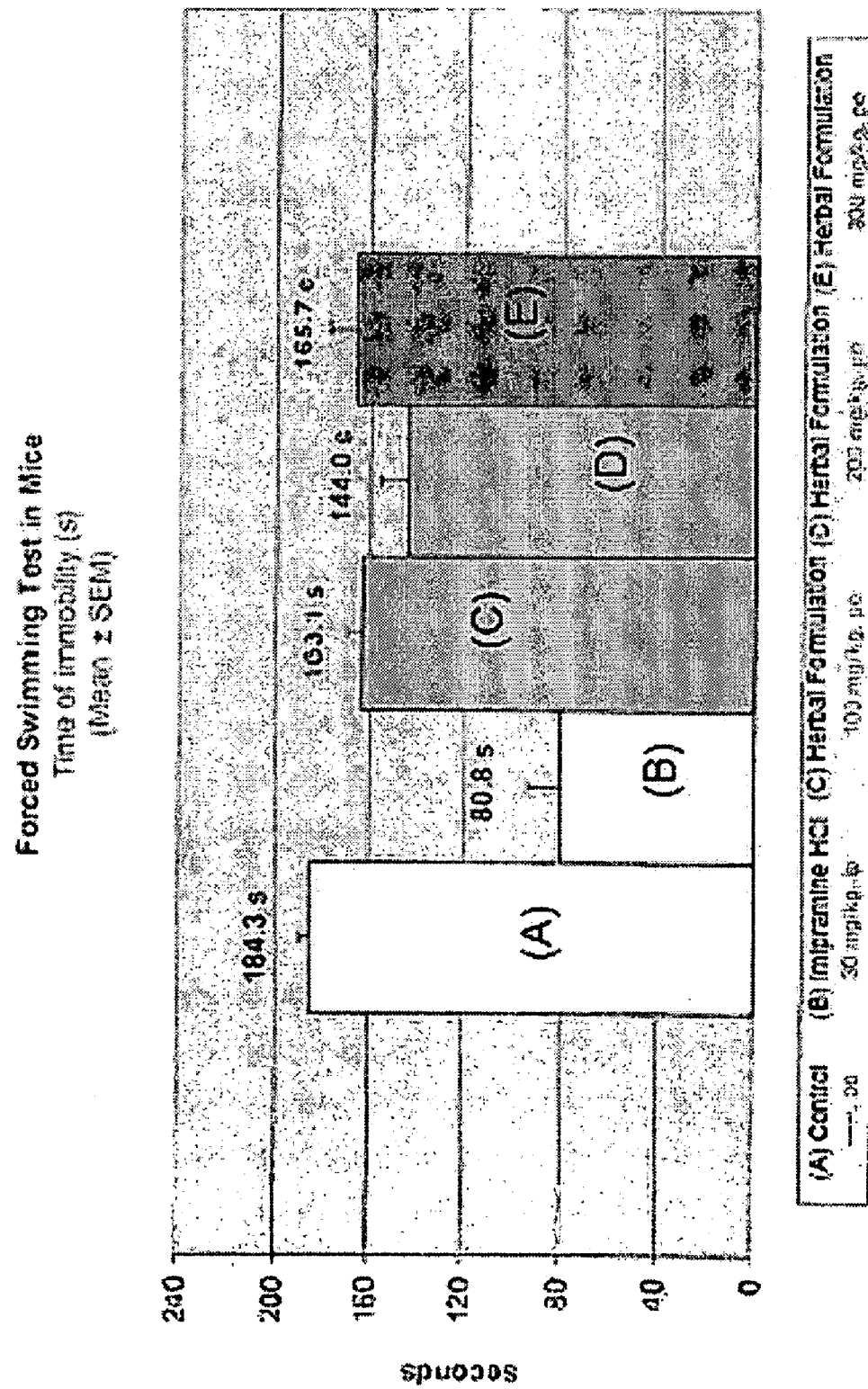
FIG. 4 is a bar diagram showing the effects of the herbal formulation on the anti-depressant activity of the mice.

Table 8 shows the overall values of the body weight and time of immobility. A graphical representation of the time of immobility is shown in FIG. 4. The corresponding individual values are shown in Tables 9 (body weight) and 10 (time of immobility).

TABLE 8

Forced Swimming Test in Mice
Global values (Mean ± SEM, n = 10)

| Treatment Dose (mg/kg) | Group | Admin. Route | Body weight (g) | Time of immobility (s) | % decrease versus Control | |
|---|---|---|---|---|---|---|
| Control | A | po | 22.6 ± 0.37 | 184.3 ± 5.72 | | |
| Imipramine HCl 30 mg/kg | B | ip | 22.4 ± 0.37 | 80.8 ± 13.14 | 56.2 | * |
| Herbal Formulation 100 mg/kg | C | po | 22.4 ± 0.27 | 163.1 ± 6.27 | 11.5 | |
| Herbal Formulation 200 mg/kg | D | po | 22.5 ± 0.31 | 144.0 ± 11.87 | 21.9 | * |
| Herbal Formulation 300 mg/kg | E | po | 22.4 ± 0.48 | 165.7 ± 11.21 | 10.1 | |
| one Way-ANOVA | | | N.S. | $p < 0.01$ | | |
| S-N-K test ($p < 0.05$) | | | | B D C E A | | |

* Differences versus Control group

TABLE 9

Forced Swimming Test in Mice Body weight (g) individual values

| animal no. | Control po | Imipramine HCl 30 mg/kg ip | Herbal Formulation 100 mg/kg po | Herbal Formulation 200 mg/kg po | Herbal Formulation 300 mg/kg po |
|---|---|---|---|---|---|
| 1 | 22 | 22 | 22 | 22 | 22 |
| 2 | 23 | 23 | 23 | 22 | 21 |
| 3 | 23 | 23 | 22 | 21 | 24 |
| 4 | 23 | 23 | 22 | 22 | 23 |
| 5 | 23 | 20 | 23 | 24 | 20 |
| 6 | 22 | 24 | 22 | 23 | 23 |
| 7 | 24 | 23 | 23 | 21 | 25 |
| 8 | 20 | 23 | 21 | 23 | 21 |
| 9 | 24 | 22 | 24 | 23 | 22 |
| 10 | 22 | 21 | 22 | 24 | 23 |
| Mean | 22.5 | 22.4 | 22.4 | 22.5 | 22.4 |
| SD | 1.17 | 1.17 | 0.64 | 1.08 | 1.51 |
| SEM | 0.37 | 0.37 | 0.27 | 0.34 | 0.48 |
| n | 10 | 10 | 10 | 10 | 10 |

TABLE 10

Forced Swimming Test in Mice
Time of immobility (s) individual values

| animal no. | Control po | Imipramine HCl 30 mg/kg ip | Herbal Formulation 100 mg/kg po | Herbal Formulation 200 mg/kg po | Herbal Formulation 300 mg/kg po |
|---|---|---|---|---|---|
| 1 | 181 | 107 | 135 | 183 | 184 |
| 2 | 184 | 90 | 149 | 165 | 155 |
| 3 | 211 | 140 | 168 | 146 | 128 |
| 4 | 203 | 111 | 168 | 118 | 167 |
| 5 | 157 | 114 | 178 | 86 | 183 |
| 6 | 184 | 64 | 156 | 145 | 172 |
| 7 | 155 | 51 | 153 | 185 | 216 |
| 8 | 176 | 3 | 143 | 144 | 211 |
| 9 | 195 | 91 | 180 | 183 | 135 |
| 10 | 196 | 37 | 201 | 85 | 106 |
| Mean | 184.3 | 80.8 | 163.1 | 144.0 | 165.7 |
| SD | 15.07 | 41.55 | 19.82 | 37.55 | 35.43 |
| SEM | 5.72 | 13.14 | 6.27 | 11.87 | 11.21 |
| n | 10 | 10 | 10 | 10 | 10 |

No statistically significant differences were detected for the body-weight values between the different treatment groups (one-way ANOVA, p<0.01).

The administration of the reference item at the dose of 30 mg/kg by intraperitoneal route induced a marked decrease in the time of immobility (56.2%) in comparison with the Control group, and these differences were statistically significant with respect to said Control group (S-N-K test, p<0.05).

The administration of the test item at the doses of 100, 200 and 300 mg/kg by oral route produced a decrease in the time of immobility of 11.5%, 21.9% and 10.1%, respectively, when compared with the Control group. The only statistically significant differences with respect to the Control group were for the test item at the dose of 200 mg/kg. However, the decrease in the time of immobility was clearly lower than that observed in the group treated with the reference item (significant differences between these two groups were obtained, S-N-K test, p<0.05). Since the reference item was administered by the intraperitoneal route, a higher dosage as compared to the test item (by oral route) would be resulted.

In conclusion, under the experimental conditions, certain antidepressant activity of the test item is observed at the dose of 200 mg/kg (administrated by oral route), although less than that obtained from the group treated with the reference item at the dose of 30 mg/kg (administrated by intraperitoneal route).

In addition, there were no statistically significant differences between the mean values obtained after the administration of the test item at the doses of 100, 200 and 300 mg/kg, and a clear dose-effect relationship was not observed under the experimental conditions. On the other hand, the results from the time of immobility suggested that the optimal dosage to be 200 mg/kg.

EXAMPLE 7

Clinical Observation of Patients Treated with the Formulation of Table 2

Two patients, suffering from depression or anxiety related disorder, took part in a study with particulars listed in the Table 11 below:

TABLE 11

|  | Patients | |
| --- | --- | --- |
|  | 1 | 2 |
| Age | 35 | 38 |
| Gender | Female | Female |
| Profile | Depression due to marital problems | Pruritis with no apparent reasons, but presumable to be anxiety-related |
| Dosage of Treatment | Two Capsules twice a day | Two Capsules once a day |
| Duration of Treatment | Three weeks | Three weeks |

In this study, the capsules taken by the patients were based on the composition of the herbal formulation listed in Table 2. Upon treatment, the first patient resumed fully back to normal, while the second patient had significant improvement over her pruritis problem.

EXAMPLE 8

Alternative Composition of the Herbal Formulation

In a variation of the preferred embodiment described above, an alternative composition of the herbal formulation is listed in Table 12 in which Radix Et. Rhizoma Glycyrrhizae Praeparata Cum Melle is not included in this composition.

TABLE 12

| No. | Herb | Composition (kg) | By weight % |
| --- | --- | --- | --- |
| 1 | Os Draconis | 4.500 | 17.86 |
| 2 | Concha Ostreae | 3.150 | 12.50 |
| 3 | Fructus *Tritici Aestivi* | 4.500 | 17.86 |
| 4 | Bulbus Lilii | 2.250 | 8.93 |
| 5 | Radix *Rehmanniae* | 2.250 | 8.93 |
| 6 | Caulis *Polygoni Multiflori* | 2.250 | 8.93 |
| 7 | Fructus Jujubae | 2.250 | 8.93 |
| 8 | Flos *Albiziae* | 1.350 | 5.36 |
| 9 | Sclerotium Poriae Circum Radicem Pini | 1.350 | 5.36 |
| 10 | Caulis *Bambusae* in Taenia | 0.675 | 2.67 |
| 11 | Rhizoma *Zingiberis Recens* | 0.675 | 2.67 |
|  | Total | 25.200 | 100.00 |

The method for preparing the herbal formulation with this alternative composition is nearly identical to that for preparing the formulation with the composition listed in Table 2, except for an extra step in the first extraction 20b. Upon putting the remaining herbs of Fructus Tritici Aestivi, Bulbus Lilii, Radix Rehmanniae, Caulis Polygoni Multiflori, Fructus Jujubae, Flos Albiziae, Sclerotium Poriae Circum Radicem Pini, Caulis Bambusae in Taenia, and Rhizoma Zingiberis Recens into the percolator with the initial herbal mixture of Os Draconis and Concha Ostreae already being inside, the percolator is filled with water at a ratio of 1:2, total ingredients:water, (i.e. for each 100 kg total ingredients, 200 liters water is used) before the mixture is boiled and simmered.

EXAMPLE 9

Clinical Observation of Patients Treated with the Formulation of Table 12

There were 20 patients taking part in this study who suffered from Post Traumatic Stress Disorder or Seasonal Affective Disorder. The particulars of the patients are listed in Table 13 below.

TABLE 13

| Age of Patients | >45 |
| --- | --- |
| Gender of Patients | 11 female/9 male |
| Profile of Patients | 5/20 were never on any antidepressants |
|  | 15/20 had taken SSRIs before Insomnia or Hypersomnia in most patients |
|  | 12/20 Fatigue |
|  | 10/20 feel worthless or guilt |
|  | 15/20 difficult to concentrate |
|  | 20% ~4/20 had thought of contemplating suicide |
| Dosage of Treatment | One capsule three times daily |
| Duration of Treatment | Two weeks |
| Co-administration of Western Medicine if any | No |

In this study, the capsules taken by the patients were based on the composition of the herbal formulation listed in Table 12 of EXAMPLE 8.

Table 14 shows the results of this study and the observations were made after 2 weeks of treatment. In short, about 75% of the patients experienced improved ability to cope with activities of daily living, while 90% of the patients had improved motivation/energy.

TABLE 14

Observations after 2 weeks of treatment:

1. Improvement of complaints of mood disorder in 70% of patients (14/20)
2. Improvement of ability to cope with activities of daily living in 75% of patients (15/20)
3. Improvement in motivation/energy in 90% of patients (18/20)
4. Improvement of sexual appetite in 20% of patients (4/20)
5. Improvement in general appearance in 90% of patients (18/20)

The preferred embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, this formulation can be taken orally in different forms such as powder, capsule or liquid. The concentration and drying steps to produce powders are therefore preferred but not essential to the present invention. In the preferred embodiment, the first extraction (steps 20a and 20b as shown in FIG. 1) describes Os Draconis and Concha Ostreae as being extracted first, but the present invention may also be practiced with all the ingredients being extracted together in a single extraction. Further, Dextrin is used as an excipient of the formulation but it is clear that other binders and/or fillers can also be employed.

What is claimed is:

1. An herbal formulation for treating depression or anxiety disorders comprising effective amounts of water extracts, obtained from:
   a) Fructus Tritici Aestivi;
   b) Bulbus Lilii;
   c) Radix Rehmanniae;
   d) Caulis Polygoni Multiflori;
   e) Fructus Jujubae;
   f) Flos Albiziae;
   g) Sclerotium Poriae Circum Radicem Pini; and
   h) Rhizoma Zingiberis Recens.

2. The herbal formulation of claim 1 further comprising Os Draconis.

3. The herbal formulation of claim 2 further comprising Concha Ostreae.

4. The herbal formulation of claim 3 further comprising Caulis Bambusae in Taenia.

5. The herbal formulation of claim 4 further comprising Radix Et. Rhizoma Glycyrrhizae Praeparata Cum Melle.

6. The herbal formulation of claim 5 wherein said formulation is suitable to be orally administered for the treatment of depression or anxiety disorders.

7. The herbal formulation of claim 5 wherein the concentration of
   a) said Os Draconis ranges from about 5 weight percent to about 15 weight percent of the formulation;
   b) said Concha Ostreae ranges from about 5 weight percent to about 15 weight percent of the formulation;
   c) said Fructus Tritici Aestivi ranges from about 10 weight percent to about 30 weight percent of the formulation;
   d) said Bulbus Lilii ranges from about 5 weight percent to about 15 weight percent of the formulation:
   e) said Radix Rehmanniae ranges from about 5 weight percent to about 15 weight percent of the formulation;
   f) said Caulis Polygoni Multiflori ranges from about 5 weight percent to about 15 weight percent of the formulation;
   g) said Fructus Jujubae ranges from about 5 weight percent to about 15 weight percent of the formulation;
   h) said Flos Albiziae ranges from about 3 weight percent to about 10 weight percent of the formulation;
   i) said Radix Et. Rhizoma Glycyrrhizae Praeparata Cum Melle ranges from about 3 weight percent to about 10 weight percent of the formulation;
   j) said Sclerotium Poriae Circum Radicem Pini ranges from about 2 weight percent to about 8 weight percent of the formulation;
   k) said Caulis Bambusae in Taenia ranges from about 1 weight percent to about 6 weight percent of the formulation; and
   l) said Rhizoma Zingiberis Recens ranges from about 1 weight percent to about 6 weight percent of the formulation.

8. The herbal formulation of claim 7 wherein said herbal formulation is water soluble.

9. The herbal formulation of claim 7 wherein said formulation is suitable to be orally administered for the treatment of depression or anxiety disorders.

10. The herbal formulation of claim 7 wherein the concentration of
    a) said Os Draconis ranges from about 8 weight percent to about 12 weight percent of the formulation;
    b) said Concha Ostreae ranges from about 8 weight percent to about 12 weight percent of the formulation;
    c) said Fructus Tritici Aestivi ranges from about 15 weight percent to about 25 weight percent of the formulation;
    d) said Bulbus Lilii ranges from about 8 weight percent to about 12 weight percent of the formulation;
    e) said Radix Rehmanniae ranges from about 8 weight percent to about 12 weight percent of the formulation;
    f) said Caulis Polygoni Multiflori ranges from about 8 weight percent to about 12 weight percent of the formulation;
    g) said Fructus Jujubae ranges from about 8 weight percent to about 12 weight percent of the formulation;
    h) said Flos Albiziae ranges from about 4 weight percent to about 8 weight percent of the formulation;
    i) said Radix Et. Rhizoma Glycyrrhizae Praeparata Cum Melle ranges from about 4 weight percent to about 8 weight percent of the formulation;
    j) said Sclerotium Poriae Circum Radicem Pini ranges from about 3 weight percent to about 6 weight percent of the formulation;
    k) said Caulis Bambusae in Taenia ranges from about 2 weight percent to about 5 weight percent of the formulation; and
    l) said Rhizoma Zingiberis Recens ranges from about 2 weight percent to about 5 weight percent of the formulation.

11. The herbal formulation of claim 10 wherein said herbal formulation is water soluble.

12. The herbal formulation of claim 10 wherein said formulation is suitable to be orally administered for the treatment of depression or anxiety disorders.

13. The herbal formulation of claim 10 wherein the concentration of
  a) said Os Draconis is about 10 weight percent of the formulation;
  b) said Concha Ostreae is about 10 weight percent of the formulation;
  c) said Fructus Tritici Aestivi is about 20 weight percent of the formulation;
  d) said Bulbus Lilii is about 10 weight percent of the formulation;
  e) said Radix Rehmanniae is about 10 weight percent of the formulation;
  f) said Caulis Polygoni Multiflori is about 10 weight percent of the formulation;
  g) said Fructus Jujubae is about 10 weight percent of the formulation;
  h) said Flos Albiziae is about 5 weight percent of the formulation;
  i) said Radix Et. Rhizoma Glycyrrhizae Praeparata Cum Melle is about 5 weight percent of the formulation;
  j) said Sclerotium Poriae Circum Radicem Pini is about 4 weight percent of the formulation;
  k) said Caulis Bambusae in Taenia is about 3 weight percent of the formulation; and
  l) said Rhizoma Zingiberis Recens is about 3 weight percent of the formulation.

14. The herbal formulation of claim 13 wherein said herbal formulation is water soluble.

15. The herbal formulation of claim 13 wherein said formulation is suitable to be orally administered for the treatment of depression or anxiety disorders.

16. A method of preparing an herbal formulation for treating depression or anxiety disorders comprising Os Draconis, Concha Ostreae, Fructus Tritici Aestivi, Bulbus Lilii, Radix Rehmanniae, Caulis Polygoni Multiflori, Fructus Jujubae, Flos Albiziae, Radix Et. Rhizoma Glycyrrhizae Praeparata Cum Melle, Sclerotium Poriae Circum Radicem Pini, Caulis Bambusae in Taenia and Rhizoma Zingiberis Recens, said method comprising
  a) extracting said Os Draconis, said Concha Ostreae, said Fructus Tritici Aestivi, said Bulbus Lilii, said Radix Rehmanniae, said Caulis Polygoni Multiflori, said Fructus Jujubae, said Flos Albiziae, said Radix Ft. Rhizoma Glycyrrhizae Praeparata Cum Melle, said Sclerotium Poriae Circum Radicem Pini, said Caulis Bambusae in Taenia and said Rhizoma Zingiberis Recens with boiling water; and
  b) concentrating said extract to form an herbal formulation.

17. A method of preparing an herbal formulation for treating depression or anxiety disorder comprising the steps of:
  a) boiling Os Draconis and Concha Ostreae in water to form an initial herbal mixture;
  b) simmering said initial herbal mixture of step (a);
  c) extracting said initial herbal mixture of step (b);
  d) boiling Fructus Tritici Aestivi, Bulbus Lilii, Radix Rehmanniae, Caulis Polygoni Multiflori, Fructus Jujubae, Flos Albiziae, Radix Et. Rhizoma Glycyrrhizae Praeparata Cum Melle, Sclerotium Poriae Circum Radicem Pini, Caulis Bambusae in Taenia and Rhizoma Zingiberis Recens with said initial herbal mixture of step (c) to form an herbal mixture;
  e) simmering said herbal mixture of step (d);
  f) extracting said herbal mixture of step (e); and
  g) filtering said herbal mixture of step (f) to form a first herbal residue and a first herbal filtrate.

18. The method of claim 17 further comprising the step of:
  a) boiling said first herbal residue in water;
  b) simmering said first herbal residue of step (a);
  c) extracting said first herbal residue of step (b); and
  d) filtering said first herbal residue of step (c) to form a second herbal filtrate and a second herbal residue.

19. The method of claim 18 wherein said first herbal filtrate is mixed with said second herbal filtrate to form a mixed filtrate.

20. The method of claim 19 wherein said mixed filtrate is concentrated to form a paste.

21. The method of claim 20 further comprising the step of mixing said paste with an excipient.

22. The method of claim 21 wherein said paste is dried.

23. The method of claim 22 wherein said dried paste is processed into a formulation suitable for oral administration.

* * * * *

UNITED STATES PATENT AND TRADEMARK OFFICE
CERTIFICATE OF CORRECTION

| | | |
|---|---|---|
| PATENT NO. | : 7,318,939 B2 | Page 1 of 1 |
| APPLICATION NO. | : 11/429247 | |
| DATED | : January 15, 2008 | |
| INVENTOR(S) | : Hei Ling Helen Chan | |

It is certified that error appears in the above-identified patent and that said Letters Patent is hereby corrected as shown below:

In Column 15, line 43 (Claim 16 (a)) of aforesaid patent, the term "Radix Ft. Rhizoma Glycyrrhizae Praeparata Cum Melle" should read as --Radix Et. Rhizoma Glycyrrhizae Praeparata Cum Melle--.

Signed and Sealed this

Eighth Day of July, 2008

JON W. DUDAS
*Director of the United States Patent and Trademark Office*